United States Patent [19]

Boschetti et al.

[11] 4,048,377
[45] Sept. 13, 1977

[54] DRIED REHYDRATABLE FILM CONTAINING AGAROSE OR GELOSE AND PROCESS FOR PREPARING SAME

[75] Inventors: Egisto Boschetti, Chatou; Yvette Paule Nicole Moroux, Mitry Mory; René Tixier, Paris, all of France

[73] Assignee: Produits Chimiques Ugine Kuhlmann, Paris, France

[21] Appl. No.: 648,084

[22] Filed: Jan. 12, 1976

[30] Foreign Application Priority Data

Jan. 14, 1975  France .................................. 75.00922

[51] Int. Cl.$^2$ ........................ B32B 27/08; C08L 5/00; C08L 5/12
[52] U.S. Cl. ............................ 428/474; 260/17.4 SG; 260/17.4 ST; 428/483
[58] Field of Search ................ 260/17.4 ST, 17.4 SG; 428/355, 483, 474

[56] References Cited
PUBLICATIONS

Chem. Absts. 71(1969) 33749v, "Acrylamide-Agarose mixed gels", Uriel
Chem. Absts. 74(1971) 91619a "Electroosmotic-agarose-stabilizing agent-electrofocussing, Quast".
Chem. Absts. 69(1968) 61812N, "Mixed Acrylamide-agarose gels", Uriel.

Primary Examiner—Edward M. Woodberry
Attorney, Agent, or Firm—Beveridge, De Grandi, Kline & Lunsford

[57] ABSTRACT

Dried agarose or gelose-containing films which are rehydratable into aqueous gel films are disclosed. The dried films are prepared by first forming, on a support, an aqueous gel film containing at most 5% by weight of agarose or gelose and a water-soluble linear polymer or copolymer of acrylamide or methacrylamide. The viscosity of such polymer and copolymer in a 5% aqueous solution at 22° C is about 17000 centipoises or less and preferably about 6000 centipoises or less. The aqueous gel film is then dried according to known techniques, with the linear polymer or copolymer of acrylamide or methacrylamide being included in the dried film.

17 Claims, No Drawings

DRIED REHYDRATABLE FILM CONTAINING AGAROSE OR GELOSE AND PROCESS FOR PREPARING SAME

The present invention has for its object a process of preparing dried films containing agarose or gelose, which films can be stored for an extended period of time and can be subsequently rehydrated into films of aqueous gels of agarose or gelose for use in immunodiffusion, electrophoresis, immunoelectrophoresis and immunoelectrodiffusion techniques and processes. The invention also relates to the dried films obtained with this process.

Agarose and gelose are polysaccharides which have been used in the form of sheets or films of aqueous gels in the techniques mentioned above. Such films contain only a slight amount of agarose or gelose (content less than or equal to 5%). The preparation of these films at the time they are to be used is troublesome because the user must first dissolve the polysaccharide in hot water and then pour the solution obtained onto a glass slide. An aqueous gel layer having a thickness of about 2 mm is formed upon cooling. Finally the user must make the necessary holes or grooves on the surface of the film for the depositing therein of the serum or immunizing serum. Furthermore, the aqueous gel sheets produced in this manner are fragile, which makes their handling and storage a delicate operation.

For this reason, there has been interest in any process which would make it possible to obtain films in a form such that they would be easy to handle and to store and which would permit one, by a simple treatment, to convert the film into an aqueous gel film of agarose or gelose, ready for use in any of the above techniques.

It has been suggested that the agarose or gelose films should be formed and stored in the dehydrated state, but then it is not possible to satisfactorily regenerate by rehydration the aqueous gel sheets or films.

It is known in the art, according to French Pat. No. 1,483,742, how to prepare mixed gel films containing, in the aqueous state, 3% to 7% of a reticulated polyacrylamide and about 1% agarose or gelose. By incorporating glycerin therein at the time of formation of the aqueous gel, the resulting dried film would be rehydratable. However, this patent does not disclose the manner of dehydration and rehydration nor the length of time nor the conditions under which the dehydrated sheets may be stored. Furthermore, in the case of simple gel films of agarose or gelose, the incorporation of glycerin at the time of formation of the aqueous gel does not make it possible to obtain films which can be rehydrated after dehydration.

The present invention has for it object a solution to the problem of forming, from aqueous gel film containing at most 5% by weight agarose or gelose, a dried film that is easy to handle and store and at the same time is totally rehydratable even after an extended period of storage time, to again form an aqueous gel film of agarose or gelose, ready for use in any of the aforementioned techniques or processes.

According to the present invention, it has been found that such rehydratable films or sheets can be formed if there is incorporated in the agarose or gelose-containing aqueous gel, prior to drying by any known process, a water-soluble linear polymer or copolymer of acrylamide or methacrylamide, whose viscosity in a 5% aqueous solution at a temperature of 22° C, is 17000 centipoises or less, and preferably, 6000 centipoises or less.

As water-soluble linear copolymers of acrylamide or methacrylamide that can be used for the purpose of this invention, there can be cited, for example, linear copolymers of acrylamide or methacrylamide with vinylpyrrolidone and linear copolymers of acrylamide or methacrylamide with an acrylic or methacrylic ester, such as monomethacrylate or the acrylate of ethylene glycol. The percentage by weight of acrylamide or methacrylamide of the linear copolymers is, preferably, at least equal to 30%.

The process according to the invention consists in preparing a hot glycero-aqueous solution containing by weight 2-3% glycerol. The solution also has therein the desired amounts of agarose (or gelose) and of linear polymer or copolymer of acrylamide or methacrylamide. The solution, which is preferably at a temperature of 75° C to 80° C, is poured onto a support, to form a layer or film of desired thickness, such as for example, 2mm, and the solution is then cooled. The aqueous gel thus formed is covered with a sheet of regenerated cellulose, such as cellophane, which has been wetted with an aqueous solution of glycerol, preferably a 2% to 3% glycerol solution or wetted with an aqueous solution of glycerol and acetic acid, preferably a 2% to 3% glycerol and 3% acetic acid solution. Finally the film is dried at a temperature of less than 30° C, preferably by passing a current of air thereover. Thus, there is formed on the support and covered with a sheet of cellophane, a flexible dried film containing the agarose or gelose and the linear polymer or copolymer of acrylamide or methacrylamide. The glycerol imparts flexibility to the film, and the film has a 3% to 7% moisture content. This film is then stored in an impermeable plastic container or bag and is maintained, preferably, at a temperature of about 4° C.

The dried films thus prepared and stored have a long, extended preservation time of at least 8 months when stored at 4° C and a shelf life of at least 3 months when stored at 20° C. Furthermore, they are easy to use in any of the aforesaid techniques. All that is required is to immerse the film for several hours in a buffer solution or preferably in renewed (renouvellee) water, at ambient temperature, and the film is then completely rehydrated to form an aqueous gel film of agarose or gelose ready for immediate use. At the time of rehydration, the linear polymer or copolymer of acrylamide or methacrylamide, being soluble in water, is removed from the gel, so that there remains the aqueous gel film of agarose or gelose. Furthermore, at the time of rehydration, the cellophane sheet is detached from the film, but this latter adheres to the support which makes its further handling easy. Buffers that can be used for the rehydration process include, for example, barbital (0.005 M, pH 8.4), tris (hydroxymethyl)aminomethane (0.05 M adhjusted to pH 7.4 by HCl), and tris(hydroxymethyl)aminomethane (0.01 M adjusted to pH 8.7 by glycocoll).

Furthermore, before covering the aqueous gel with the cellophane sheet and then drying it, it is possible to make whatever holes, grooves, and the like, in the gel surface which may be necessary for subsequent use of the film, after rehydration, in the techniques of immunodiffusion, electrophoresis, immunoelectrophoresis and immunoelectrodiffusion The concentrations of agarose (or gelose) and of linear polymer or copolymer of acrylamide or methacrylamide of the glycero-aqueous solution used in the process according to the invention, and consequently the concentrations of these constitutents in the aqueous gel obtained before drying, are preferably between 0.6% and 1.5% by weight of agarose (or gelose) and between 3% and 6% by weight for the linear polymer or copolymer of acrylamide or methacrylamide.

The linear polymers or copolymers of acrylamide or methacrylamide used in the process according to the invention can be prepared, according to known methods, by polymerization or copolymerization in an aqueous medium of the monomer or monomers, in the presence of catalyst systems such as N,N,N',N' tetramethyl ethylene diamine (TEMED) and an alkaline persulfate, dimethylaminopropionitrile and an alkaline persulfate, riboflavin and an alkaline persulfate in the presence of ultra-violet (UV) rays, and 2,2'-azo-bis-isobutyronitrile. The polymer or copolymer formed is then separated by dialysis and/or precipitation in an alcohol medium, dehydrated and then dried.

The linear polymers or copolymers of acrylamide or methacrylamide used in the process according to the invention can also be prepared by an original method which offers the advantage, over the standard method described above, of providing linear polymers or copolymers whose aqueous or glycero-aqueous solutions are often clearly less viscous than those of the linear polymers or copolymers obtained by the standard methods, which facilitates the use of the products at the time of preparation of the aqueous gel sheets. According to this original method the polymerization or copolymerization of the monomer or monomers is performed, in the presence of one of the catalyst systems previously mentioned, but, instead of a pure aqueous medium, there is used an aqueous medium containing a water-soluble non-copolymerizable organic compound such as, for example, a polyol, a sugar, a polysaccharide or a polyvinylpyrrolidone. Examples of polyols that can be used include, in particular, glycols, glycerol, sorbitol and polyethylene glycols having an average molecular weight of 200 to 600. Examples of polyvinylpyrrolidones that can be used include, in particular, polyvinylpyrrolidones having an average molecular weight of 10,000 to 40,000. The weight of the water-soluble non-copolymerizable organic compound used is preferably equal to or approximate to the weight of the monomer or monomers used. The linear polymers or copolymers of acrylamide or methacrylamide thus formed are then separated, in a form free of the above organic compound, by dialysis and/or precipitation in an alcohol medium, dehydrated and dried.

As supports that can be used in the preparation of the dried sheets by the process according to the invention there can be cited, in particular, the transparent plastic supports for photographic films, based on treated polyester, known on the market by the name "Cronar Clear Base" and sold by E. I. Du Pont de Nemours and Co., Wilmington, Del. 19898, USA. It has been found that these supports possess the required adherence qualities with respect to the films of aqueous gel of agarose or gelose, contrary to other supports, such as cellulose triacetate films or ethylene glycol polyterephthalate films, known by the trademark ∓Mylar."

The following examples, while designed to illustrate the invention, are in no way to be considered as limiting the scope of the invention thereto:

EXAMPLE 1

1. Preparation of the linear acrylamide polymer

Into one liter of demineralized water at ambient temperature there are dissolved 100 g of pure crystallized acrylamide monomer and 0.2 ml of N,N,N',N' tetramethyl ethylene diamine (TEMED). The pH of the solution is adjusted to 6.8–7 with HCl, and then 0.8 g of ammonium persulfate is added. The solution is thereafter heated for 2 hours at 50° C. After cooling, the solution is first dialyzed and then the polymer is precipitated by addition of 4 volumes of methanol to the dialysate and stirring the mixture. The precipitate obtained is separated by decanting, then taken up again by methanol and dehydrated by grinding in this solvent. The polymer is then drained and dried under vacuum at 60° C. 95 to 100 g of linear acrylamide polymer are produced, in the form of a white water-soluble powder, whose viscosity, in a 5% aqueous solution at 22° C, is equal to 17000 centipoises.

2. Preparation of dried agarose (or gelose) films 2 g of agarose (or gelose) are dissolved in 100 ml of boiling demineralized water containing 2% glycerol in a boiling water bath 8 g of the linear acrylamide polymer prepared as indicated above are dissolved in 100 ml of demineralized water containing 2% glycerol at ambient temperature. The two solutions are brought to 75°–80° C and then mixed while slowly stirring to avoid the formation of air bubbles. The mixture, while at this same temperature, is then poured onto a transparent plastic support, "Cronar Clear Base C-72", which has been placed on a horizontal glass slide, and a gel layer 2 mm thick is formed. The layer is cooled to a temperature below 25° C and forms an aqueous gel that adheres to the plastic support. Holes and grooves are formed on the surface of the gel by means of an appropriate tool, and the gel that fills the holes is removed by aspiration with a Pasteur pipette. The aqueous gel film is then covered with a cellophane sheet previously wetted in a glycero-aqueous solution containing 2% glycerol. The edges of the cellophane sheet are folded under the glass slide and the unit is dried at ambient temperature in an air current over night.

The unit, which consists of the dried gel film, the "Cronar Clear Base C-72" support and the cellophane sheet is then detached from the glass slide and stored under the conditions indicated above. The dried film, thus obtained and stored, has a long storage life and is totally rehydratable.

EXAMPLE 2

1. Preparation of the linear acrylamide polymer

Into a liter of demineralized water at ambient temperature there are dissolved 100 g of pure crystallized acrylamide monomer, 100 g of powdered polyvinylpyrrolidone with a molecular weight of 11000 and 1 ml of TEMED. The pH of the solution is adjusted to 6.8–7 with N HCL and then 0.8 g of ammonium persulfate is added thereto. The solution thus formed is heated for 5 hours at 50° C and then allowed to cool to ambient temperature. The solution is then dialyzed with reference to demineralized water, and the polymer is precipitated by addition of 5 volumes of methanol to the dialysate and vigorously stirring the mixture. The precipitate obtained is separated by decanting, then taken up by methanol and dehydrated by grinding in solvent. The polymer is then drained and dried under vacuum at 60° C. 90 to 95 g of linear acrylamide polymer are produced, in the form of a white water-soluble powder, whose viscosity in 5% aqueous solution at 22° C, is less than 6000 centiposes.

2. Preparation of dried agarose (or gelose) films

The process of Example 1 is repeated except that the 8 g of linear acrylamide polymer of Example 1 are replaced by 12 g of the linear acrylamide polymer formed as described above by polymerization in the presence of polyvinylpyrrolidone having a molecular weight of 11,000.

The dried film obtained has a long storage life and is totally rehydratable.

EXAMPLE 3

1. Preparation of linear acrylamide polymer

The process of Example 2 is repeated except that the 100 g of polyvinylpyrrolidone having a molecular weight of 11,000 are replaced with 100 g of polyethyleneglycol having a molecular weight of 600 and 2 ml of TEMED are used instead of 1 ml. 90 to 95 g of linear acrylamide polymer are produced, in the form of a white water-soluble powder. Its viscosity, in 5% aqueous solution at 22° C, is less than 6000 centipoises.

2. Preparation of dried agarose (or gelose) films

The process of Example 1 is repeated except that the 8 g of linear acrylamide polymer of Example 1 are replaced by 12 g of the linear acrylamide polymer produced above by polymerization in the presence of polyethylene glycol having a molecular weight of 600.

The dried film obtained has a long storage life and is totally rehydratable.

EXAMPLE 4

1. Preparation of linear acrylamide polymer

The process of Example 2 is repeated except that the 100 g of polyvinylpyrrolidone having a molecular weight of 11,000 are replaced by 100 g of glycerol. 90 to 95 g of linear acrylamide polymer are produced, in the form of a white water-soluble powder, whose viscosity in 5% aqueous solution at 22° C, is less than 6000 centipoises.

2. Preparation of dried agarose (or gelose) films

The process of Example 1 is repeated except that the 8 g of linear acrylamide polymer of Example 1 are replaced by 12 g of linear acrylamide polymer as formed above by polymerization in the presence of glycerol.

The dried film which is produced has a long preservation time and is totally rehydratable.

EXAMPLE 5

1. Preparation of linear acrylamide polymer

The process of Example 2 is repeated except that the 100 g of polyvinylpyrrolidone having a molecular weight of 11,000 are replaced by 100 g of sorbitol. 90 to 95 g of linear acrylamide polymer are produced, in the form of a white water-soluble powder, whose viscosity in 5% aqueous solution at 22° C, is less than 17000 centipoises.

2. Preparation of dried agarose (or gelose) sheets

The operation of Example 1 is repeated except that the 8 g of linear acrylamide polymer of Example 1 are replaced by 6 g of linear acrylamide polymer as produced above by polymerization in the presence of sorbitol.

The dried film obtained has a long preservation time and is totally rehydratable.

EXAMPLE 6

1. Preparation of the linear acrylamide copolymer

To 900 ml of demineralized water at ambient temperature are added 50 g of pure crystallized acrylamide monomer and 50 ml of vinylpyrrolidone. The solution is stirred for 15 minutes and is then filtered. The filtered solution is brought to 50° C and 2 ml of TEMED are added thereto. The pH is adjusted to 6.8–7 with N HCl and then 1 g of ammonium persulfate is dissolved in the solution. The solution is kept at 50° C for 5 hours and is then cooled to ambient temperature. The solution is then dialyzed with reference to demineralized water, and the copolymer is precipitated by the addition of 10 volumes of methanol to the dialysate, while the mixture is stirred. The precipitate which forms is separated by decanting, then taken up by methanol and dehydrated by grinding in this solvent. The copolymer is then drained and dried under vacuum at 60° C. A linear copolymer of acrylamide and vinylpyrrolidone is produced in the form of a water-soluble white powder, whose viscosity in 5% aqueous solution at 22° C, is less than 6000 centipoises.

2. Preparation of dried agarose (or gelose) films

The process of Example 1 is repeated except that the 8 g of the linear acrylamide polymer of Example 1 are replaced by 12 g of acrylamide and vinylpyrrolidone linear copolymer produced above.

The dried film obtained has a long storage life and is totally rehydratable.

EXAMPLE 7

1. Preparation of linear acrylamide copolymer

The process of Example 6 is repeated except that at the start there are added 100 ml of polyethylene glycol with a molecular weight of 600. A linear copolymer of acrylamide and vinylpyrrolidone is obtained, in the form of white water-soluble powder, whose viscosity in 5% aqueous solution at 22° C, is less than 6000 centipoises.

2. Preparation of the dried agarose (or gelose) films

From the linear copolymer of acrylamide and vinylpyrrolidione produced above by copolymerization in the presence of the polyethylene glycol of a molecular weight of 600, there are prepared, by utilizing the process of Example 6, dried agarose (or gelose) films.

The dried films obtained have a long storage life and are totally rehydratable.

Having described the invention, what is claimed is:

1. A process for preparing a dried agarose or gelose-containing film rehydratable into an aqueous gel film of agarose or gelose, said process consisting essentially of the steps of:
    1. forming an aqueous gel film containing at most 5% by weight agarose or gelose and a water-soluble, linear polymer or copolymer of a member selected from the group consisting of acrylamide and methacrylamide, said polymer or copolymer having a viscosity of about 17,000 centipoises or less when in a 5% aqueous solution at a temperature of 22° C, by pouring onto a support a hot glycero-aqueous solution containing the agarose or gelose and said polymer or copolymer and cooling said solution,
    2. drying the resulting aqueous gel film, said polymer or copolymer being present in an amount sufficient to maintain said dried film in storage for an extended period of time.

2. The process as defined in claim 1 wherein said agarose or gelose is present in the aqueous gel film in an amount of 0.6% to 1.5% by weight and said linear polymer or copolymer is present in the aqueous gel film in an amount of 3% to 6% by weight.

3. The process as defined in claim 1 wherein said linear copolymer is selected from the group consisting of a copolymer of acrylamide and vinylpyrrolidone and a copolymer of methacrylamide and vinylpyrrolidone.

4. The process as defined in claim 3 wherein said acrylamide and methacrylamide are at least 30% by weight of said copolymers.

5. The process as defined in claim 1 wherein said linear polymer or copolymer is produced by polymerization or copolymerization of the monomer or monomers, in the presence of a catalyst system, in an aqueous medium containing a water-soluble non-copolymerizable organic compound.

6. The process as defined in claim 5 wherein the weight of said water-soluble non-copolymerizable organic compound is about equal to the weight of said monomer or monomers.

7. The proces as defined in claim 5 wherein said water-soluble non-copolymerizable organic compound is a member selected from the group consisting of polyol, polyvinylpyrrolidone, polysaccharide and sugar.

8. The process as defined in claim 6 wherein said polyol is polyethylene glycol having a molecular weight of 600.

9. The process as defined in claim 6 wherein said polyvinylpyrrolidone has an average molecular weight of from 10,000 to 40,000.

10. The process as defined in claim 9 wherein said polyvinylpyrrolidone has an average molecular weight of about 11,000.

11. A dried film rehydratable into an aqueous gel film of agarose or gelose and consisting essentially of agarose or gelose and a sufficient amount of a water-soluble, linear polymer or copolymer of a member selected from the group consisting of acrylamide and methacrylamide, to maintain said dried film in storage for an extended period of time, said polymer or copolymer having a viscosity of no more than 17,000 centipoises in a 5% aqueous solution at a temperature of 22° C.

12. The dried film as defined in claim 11 wherein said linear copolymer is selected from the group consisting of acrylamide-vinylpyrrolidone copolymer and methacrylamide-vinylpyrrolidone copolymer.

13. The dried film as defined in claim 11 wherein said film has a moisture content of 3% to 7%.

14. The dried film as defined in claim 11, said film being adheringly supported on a transparent, plastic support and being completely covered by a cellophane sheet extending over said film and onto the bottom of said support.

15. The dried film as defined in claim 14 wherein said transparent plastic support is a "Cronar Clear Base C-72" polyester support, and said support has the ability of adhering to said film after rehydration of said film.

16. The process as defined in claim 1 wherein said polymer or copolymer has a viscosity of less than 6000 centipoises.

17. The process as defined in claim 16 wherein said polymer or copolymer has a viscosity of from about less than 6000 centipoises to 17000 centipoises.

* * * * *